(12) United States Patent
Lam et al.

(10) Patent No.: US 7,939,711 B2
(45) Date of Patent: May 10, 2011

(54) ABIOTIC STRESS TOLERANCE CONFERRED BY J-DOMAIN CONTAINING PROTEINS

(75) Inventors: Hon-Ming Lam, Shatin (HK); Samuel Sai Ming Sun, Shatin (HK); Gui Hua Shao, Beijing (CN)

(73) Assignee: The Chinese University of Hong Kong, Hong Kong (CN)

( * ) Notice: Subject to any disclaimer, the term of this patent is extended or adjusted under 35 U.S.C. 154(b) by 859 days.

(21) Appl. No.: 11/852,992

(22) Filed: Sep. 10, 2007

(65) Prior Publication Data

US 2008/0109920 A1    May 8, 2008

Related U.S. Application Data

(60) Provisional application No. 60/843,943, filed on Sep. 11, 2006.

(51) Int. Cl.
*C12N 15/82* (2006.01)
(52) U.S. Cl. ........................................ 800/278; 435/468
(58) Field of Classification Search ........................ None
See application file for complete search history.

(56) References Cited

U.S. PATENT DOCUMENTS

| | | | | |
|---|---|---|---|---|
| 2004/0031072 | A1* | 2/2004 | La Rosa et al. | 800/278 |
| 2005/0251879 | A1 | 11/2005 | Hofius et al. | |
| 2009/0126039 | A1* | 5/2009 | Sanz Molinero | 800/278 |

FOREIGN PATENT DOCUMENTS

| | | |
|---|---|---|
| JP | 2001078603 | 3/2001 |
| LT | 5053 B | 9/2003 |
| WO | WO-01/17332 | 3/2001 |

OTHER PUBLICATIONS

Seki et al. Monitoring the expression pattern of 1300 *Arabidopsis* genes under drought and cold stresses by using a full-length cDNA microarray. (2001) The Plant Cell; vol. 13; pp. 61-72.*
Miernyk, J. A. The J-domain proteins of *Arabidopsis thaliana*: an unexpectedly large and diverse family of chaperonse. (2001) Cell Stress and Chaperones; vol. 6; pp. 209-218.*
Federoff and Ehrhardt—NASC; The European *Arabidopsis* Stock Center (2004—evidenced by AGR Insert Page.*
*Arabidopsis* Genome Resource (AGR) Insert page, JIC Inserts. (2004); pp. 1-3.*
Robinson et al. New introductions of drought tolerant plant materials for parking lots and highway medians. (1994) Proceedings of the 107th Annual Meeting of the Florida State Horticultural Society; pp. 193-196.*
Zhang et al. Transgenic salt-tolerant tomato plants accumulate salt in foliage but not in fruit. (2001) Nature Biotechnology; vol. 19; pp. 765-768).*
Wang et al. Rold of plant heat-shock proteins and molecular chaperones in the abiotic stress response (2004) Trends in Plant Science; vol. 9; pp. 244-252.*
Baszczynski et al., Maydica (1997) 42:189-201.
Bukau and Horwich, Cell (1998) 92:351-366.
Cyr et al., J. Biol. Chem. (1994) 269:9798-9804.
Ellis, Nature (1987) 328:378-379.
Futamura et al., Plant and Cell Physiology (1999) 40:524-531.
Ham et al., Plant Cell (2006) 18:2005-2020.
Hemmingsen et al., Nature (1988) 333:330-334.
Hennessy et al., Cell Stress & Chaperones (2000) 4:347-358.
Hwang et al., Journal of Biosciences (2005) 30:657-667.
Lee et al., Plant Cell (1994) 6:1889-1897.
Lee et al., Plant Journal (1995) 8:603-612.
Lithuanian Patent Document No. LT 5053B, date published on Sep. 25, 2003 (English abstract retrieved from Delphion on Jan. 17, 2008).
Liu et al., Plant Physiology and Biochemistry (2006) 44:380-386.
Miernyk, Cell Stress & Chaperones (2001) 6:209-218.
Nguyen et al., Mol. Gen. Genomics (2004) 272:35-46.
Sato and Yokoya, Plant Cell Reports (2007) DOI10.1007/s00299-007-0470-0.
Swindell et al., BMC Genomics (2007) 8:Art No. 125.
Wang et al. Trends in Plant Science 2004 9:244-252.
Wise, BMC Bioinformatics (2003) 29:52-70.
Zhu et al., Plant Cell (1993) 5:341-349.

* cited by examiner

*Primary Examiner* — Cathy Kingdon Worley
(74) *Attorney, Agent, or Firm* — Morrison & Foerster LLP

(57) ABSTRACT

The invention describes a method of enhancing the expression of nucleotide sequences encoding proteins that comprise at least a DnaJ-type J-domain, in particular GmDNJ1, in plants or plant cells. Overexpression of the proteins protects plants or plant cells from salinity, osmotic, or dehydration stress.

5 Claims, 12 Drawing Sheets

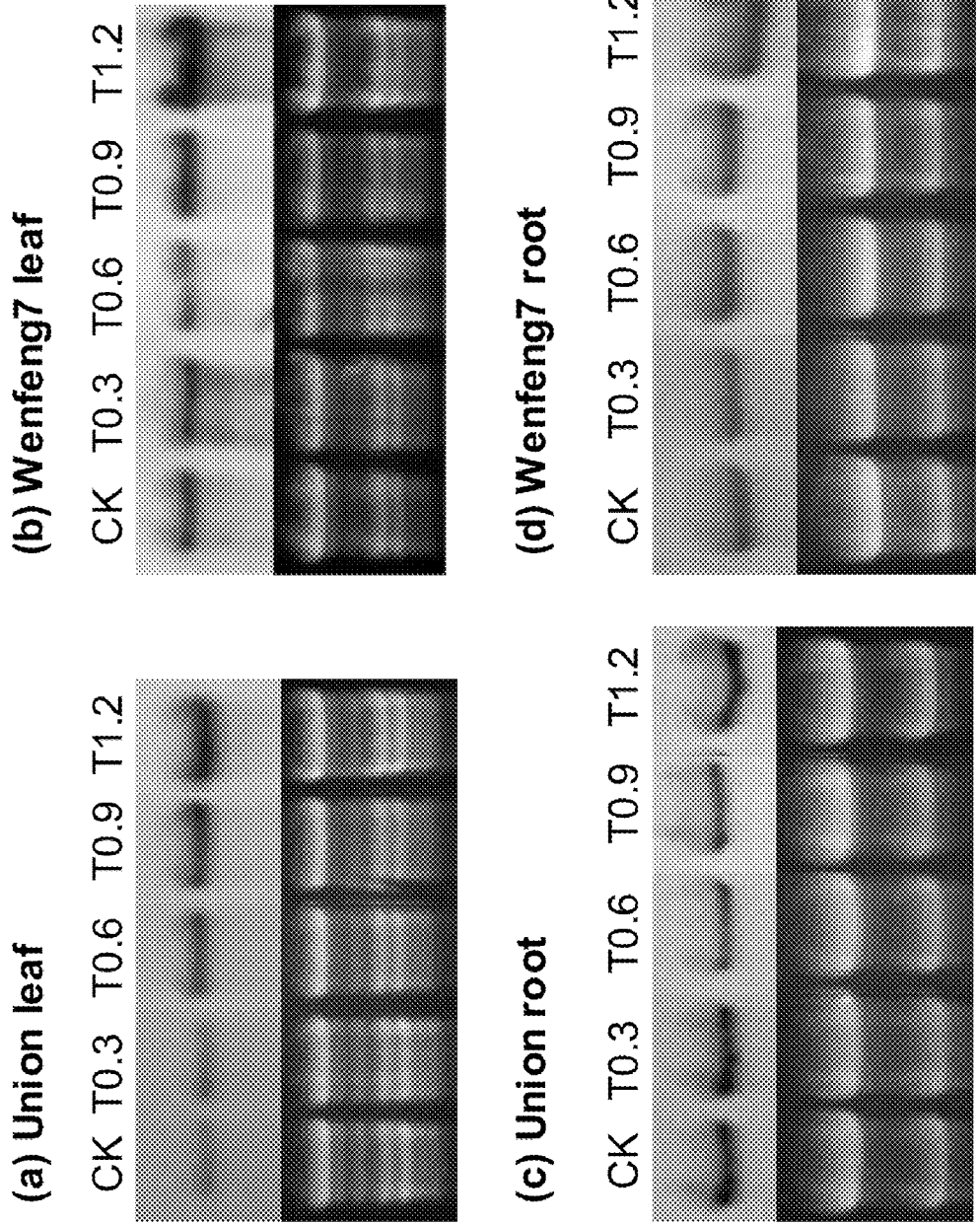
Figure 1. Northern blot analysis of *GmDNJ1* under salt stress

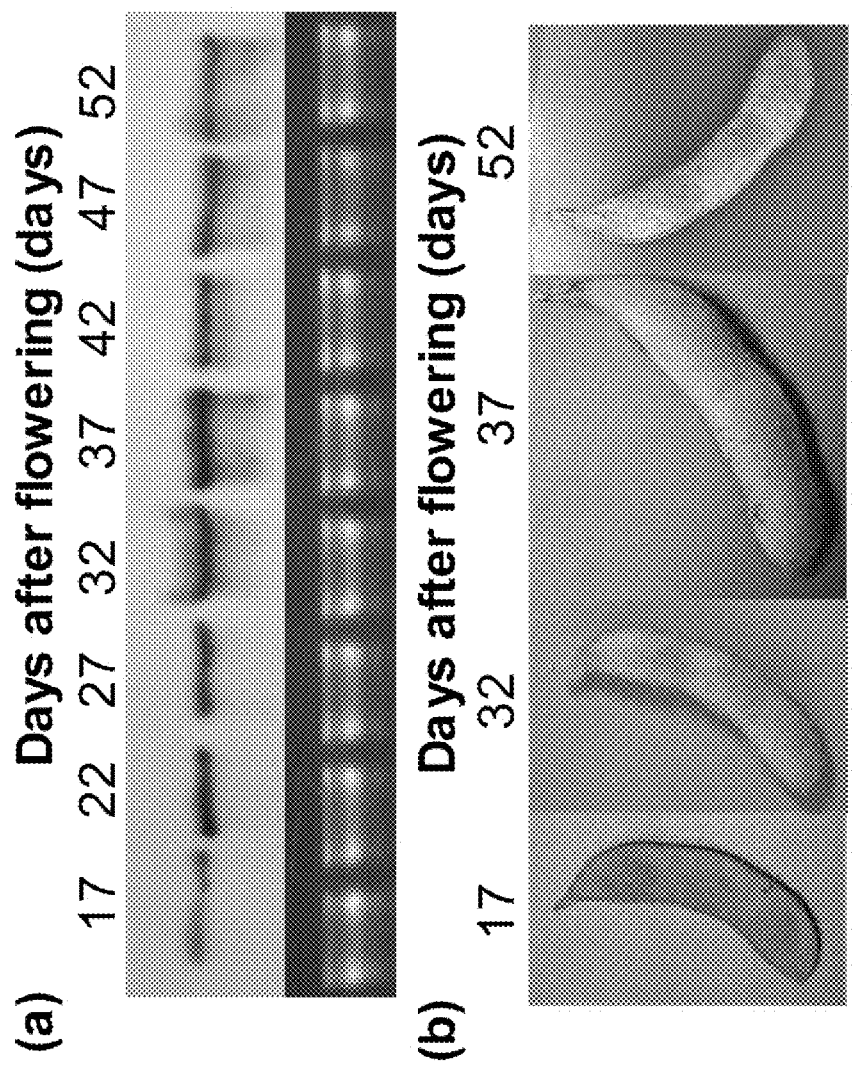
Figure 2. Northern blot analysis of *GmDNJ1* during seed maturation

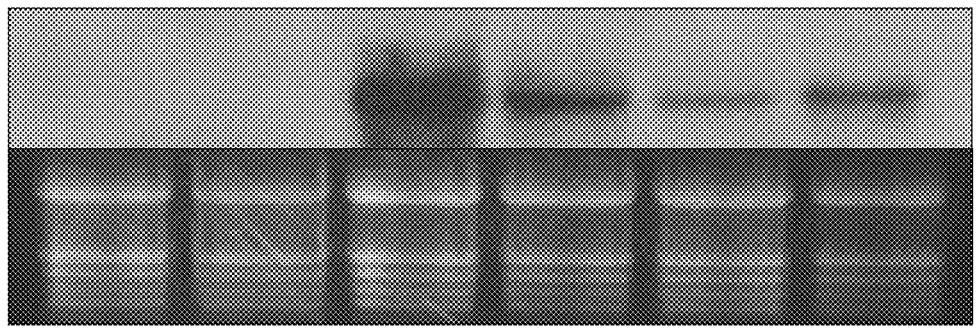
Figure 3. Northern blot analysis of the *GmDNJ1* transgene in the four Arabidopsis transgenic lines

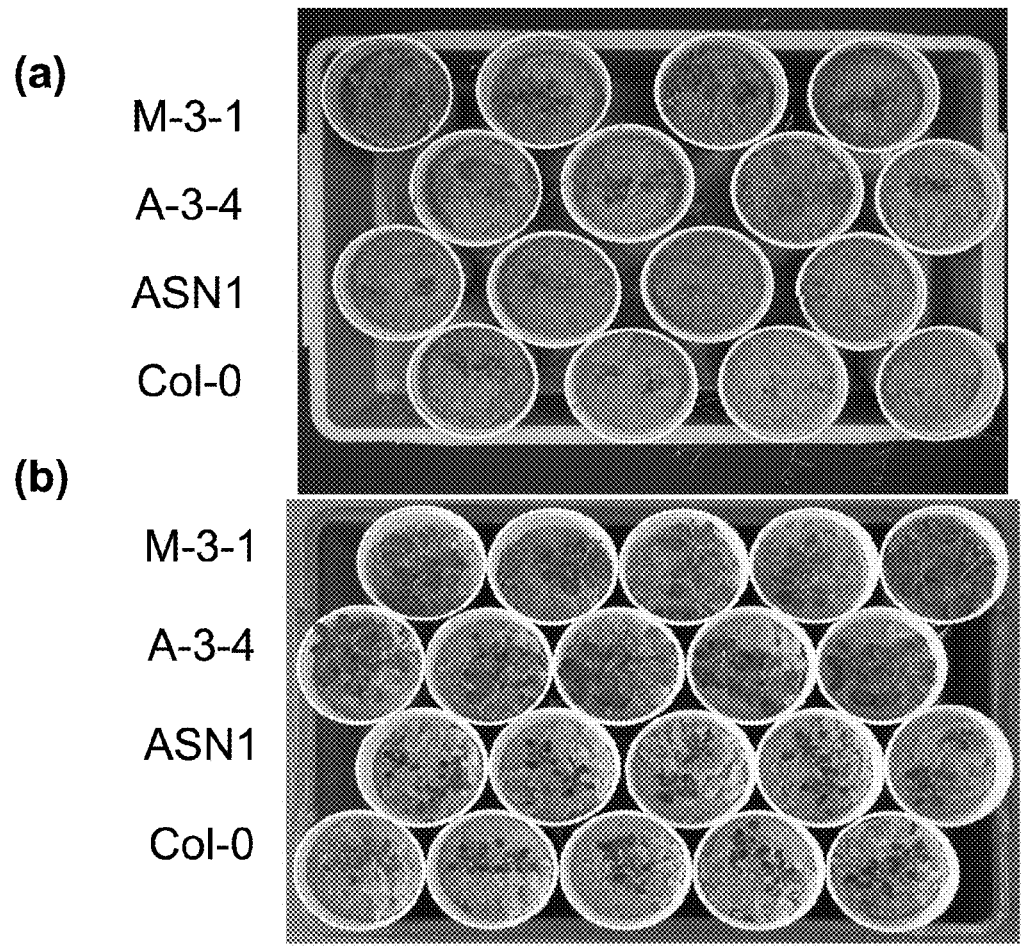
Figure 4. Appearance of Col-0, ASN1 (as a negative transgenic control), and the two *GmDNJ1* transgenic lines treated with 15% PEG (a) and 500mM NaCl (b).

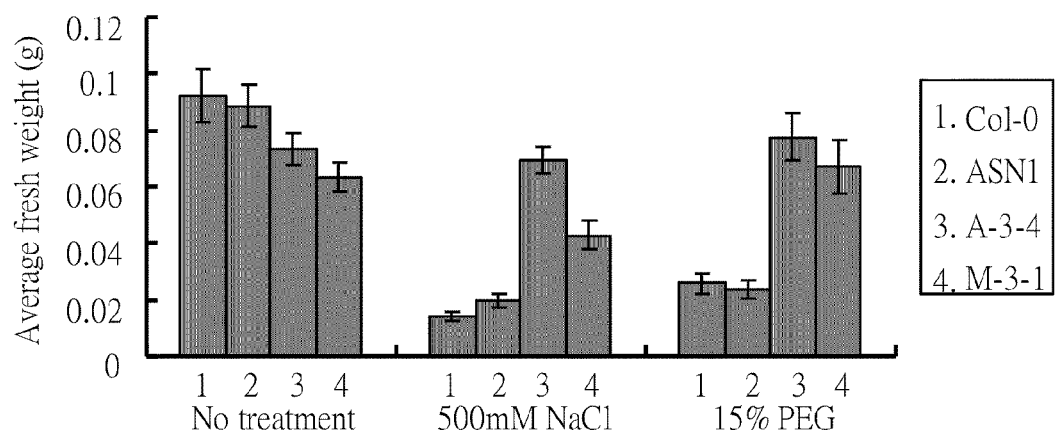
Figure 5. Fresh weight of wild type and transgenic *Arabidopsis* lines treated with 500mM NaCl or 15% PEG.

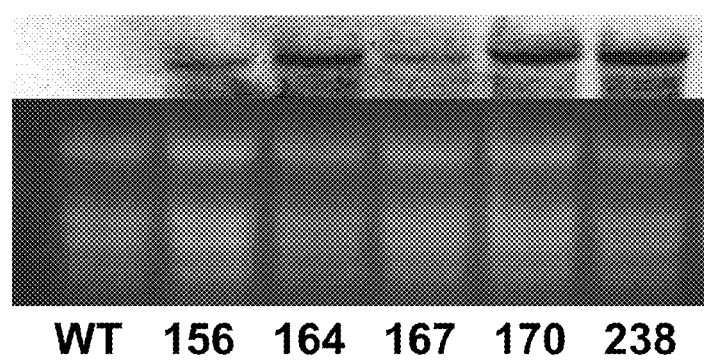
Figure 6. Northern blot analysis of the *GmDNJ1* transgene in transgenic rice

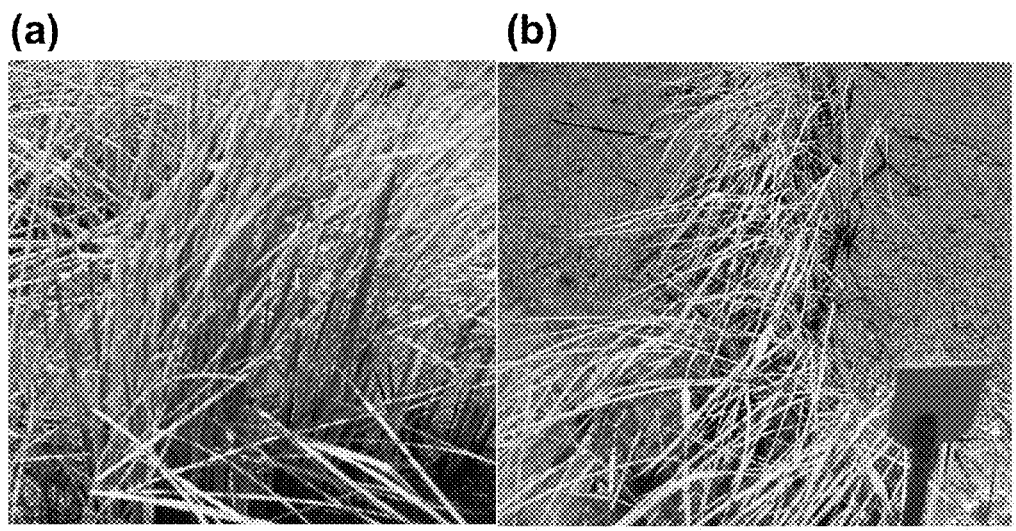
Figure 7. Appearance of *GmDNJ1* transgenic lines (segregating population) (a) and wild type rice (b) on a field with high salt contents.

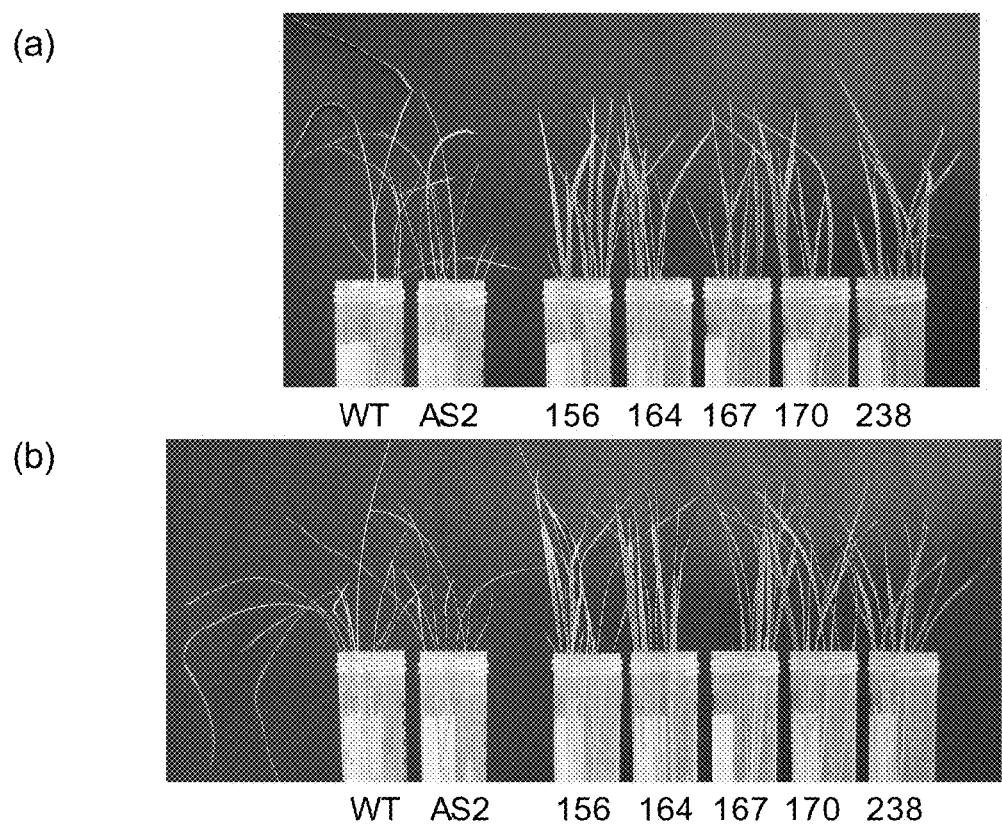
Figure 8. Appearance of untransformed and transgenic rice lines under dehydration stress

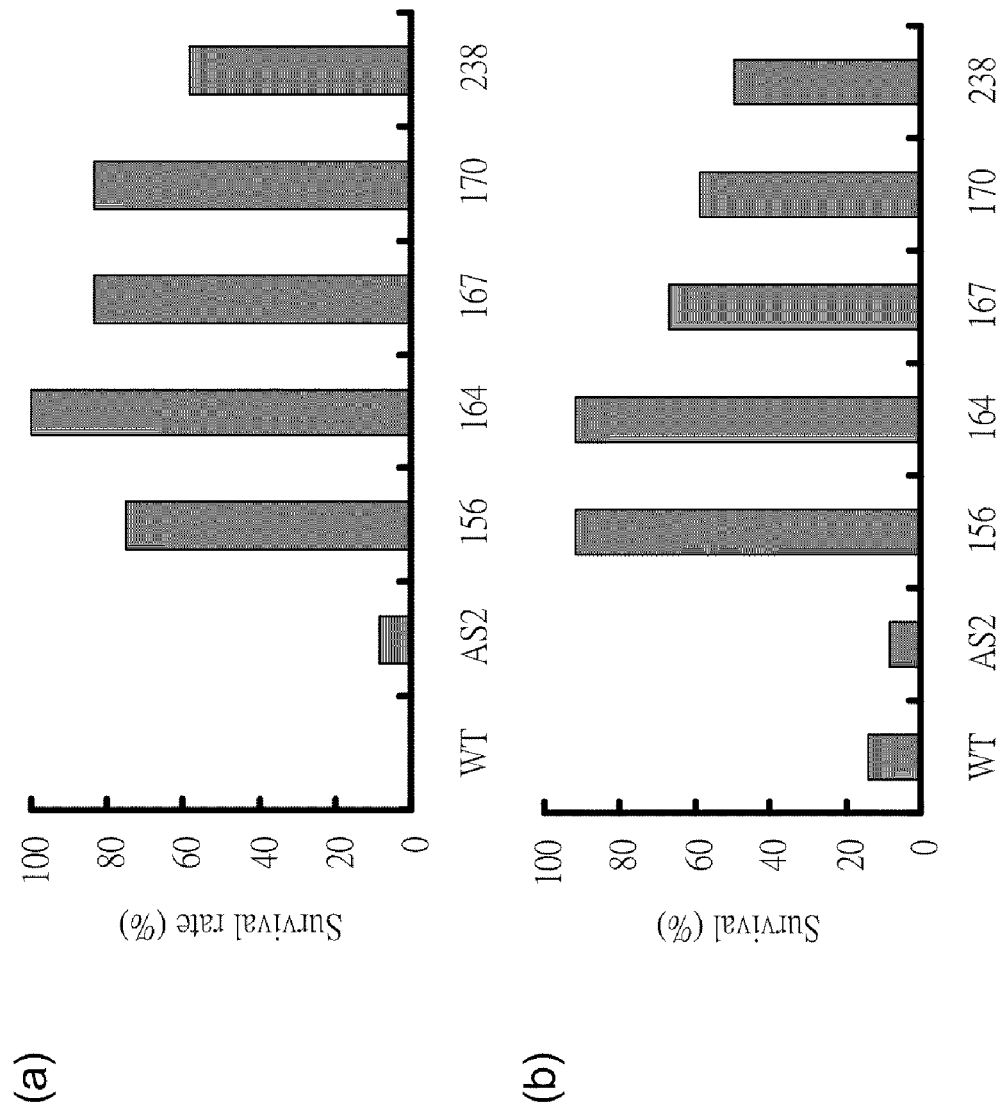
Figure 9. Survival rates of untransformed and transgenic rice lines under dehydration stress

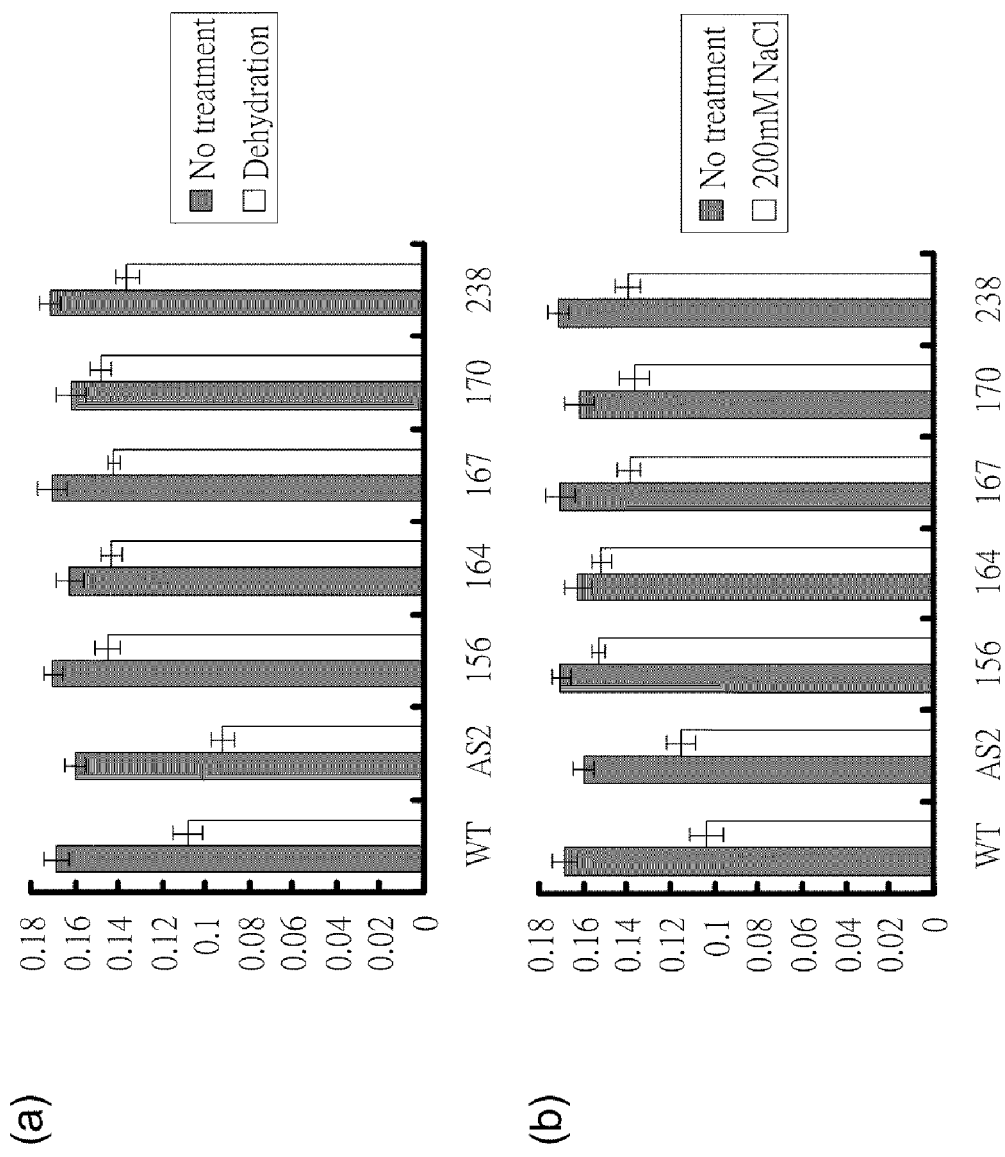
Figure 10. Fresh weight of untransformed and transgenic rice lines under dehydration stress

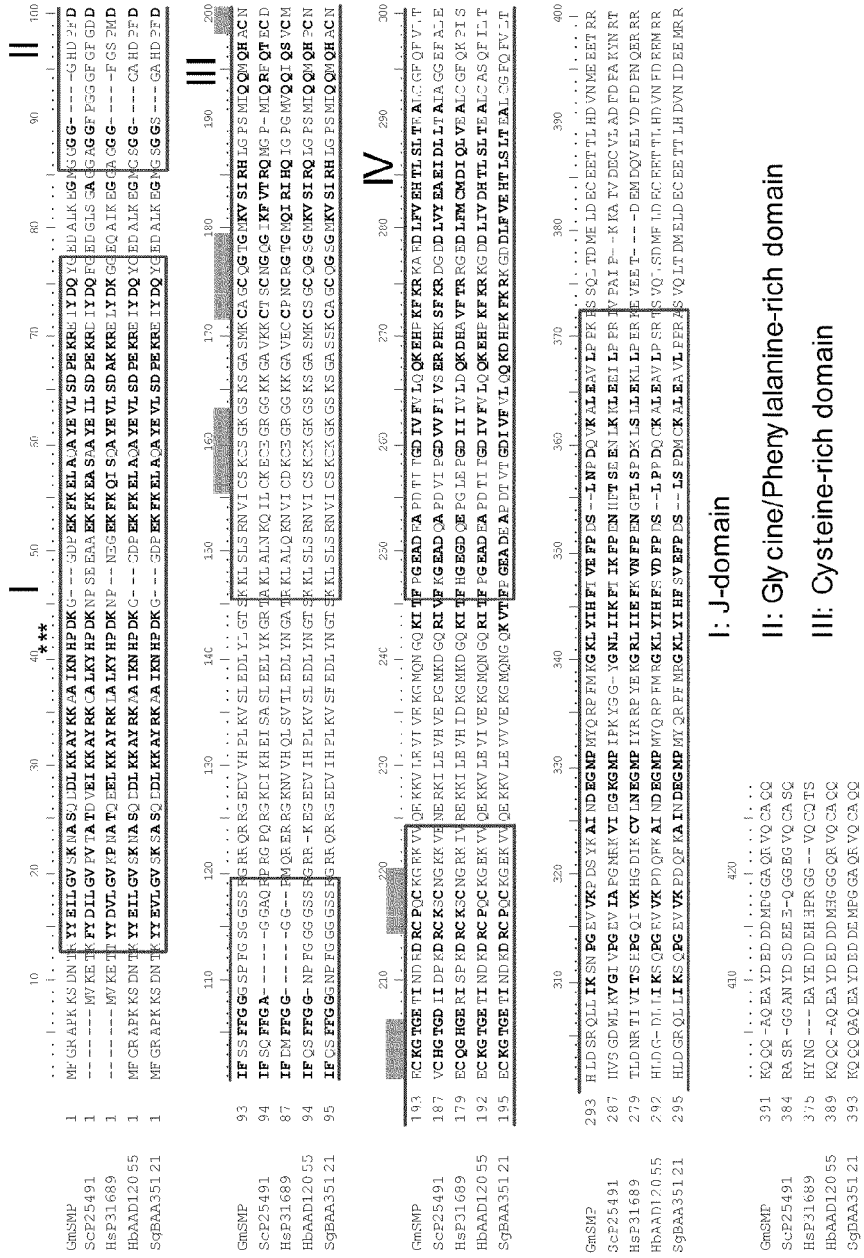
Figure 11a. Comparison of the amino acid sequence of GmDNJ1 to known DnaJ proteins.

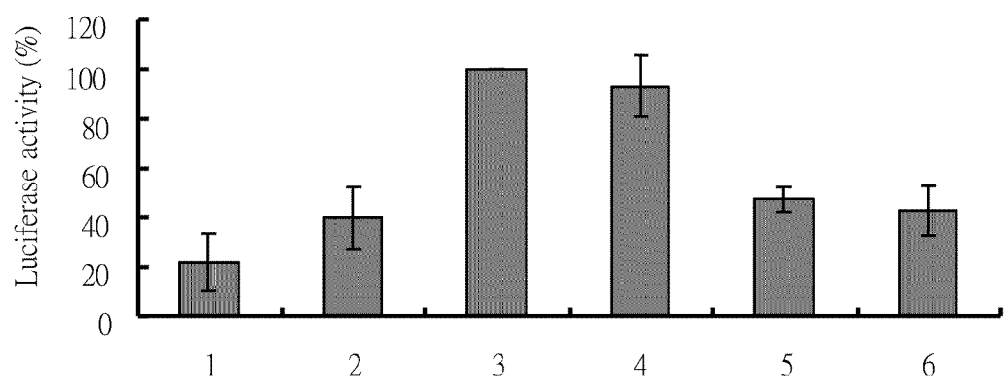
Figure 11b. Chaperone activity of GmDNJ1 expressed as relative activity of heat-denatured luciferase.

SEQUENCE LISTING

<160> NUMBER OF SEQ ID NOS: 8

<210> SEQ ID NO 1
<211> LENGTH: 32
<212> TYPE: PRT
<213> ORGANISM: Artificial Sequence -continued

```
<220> FEATURE:
<223> OTHER INFORMATION: seed maturation DnaJ protein
<220> FEATURE:
<221> NAME/KEY: ZN_FING
<222> LOCATION: (1)...(32)
<220> FEATURE:
<221> NAME/KEY: VARIANT
<222> LOCATION: 2,3,5,7,10,11,13,15,18,19,21,23,26,27,29,31
<223> OTHER INFORMATION: Xaa = any amino acid

<400> SEQUENCE: 1

Cys Xaa Xaa Cys Xaa Gly Xaa Gly Cys Xaa Xaa Cys Xaa Gly Xaa Gly
 1               5                  10                  15

Cys Xaa Xaa Cys Xaa Gly Xaa Gly Cys Xaa Xaa Cys Xaa Gly Xaa Gly
             20                  25                  30

<210> SEQ ID NO 2
<211> LENGTH: 1254
<212> TYPE: DNA
<213> ORGANISM: Artificial Sequence
<220> FEATURE:
<223> OTHER INFORMATION: Transgenic Arabidopsis thaliana
<220> FEATURE:
<223> OTHER INFORMATION: GmDNJ1 encoding sequence

<400> SEQUENCE: 2
atgtttggga gggcaccgaa gaagagcgat aatacgaggt actacgaaat cctcggcgtc      60
tccaagaacg cttcgcagga tgatctgaag aaggcttaca agaaagccgc cattaagaat     120
caccccgaca agggcggtga tcccgagaag tttaaagagc tggcgcaagc ttatgaggtt     180
ctgagtgacc ctgagaagcg tgagatatat gatcagtatg gtgaagatgc gcttaaggaa     240
ggaatgggtg gtggcggtgg ccatgatcca tttgatatct tttcatcttt ctttggcggt     300
gggagtccct ttggatcagg tggaagtagt cgaggtagga ggcagaggcg cggagaagac     360
gtggttcacc ctctcaaggt ctctttggag gacctttatc ttggaacttc caagaagctc     420
tccctctcca gaaatgttat atgctccaag tgcagtggca agggttctaa gtctggtgct     480
tcgatgaagt gtgctggttg tcaaggaact ggtatgaagg tttctataag acatcttggc     540
ccatccatga ttcagcaaat gcagcatgcc tgcaatgaat gtaagggtac tggagaaact     600
atcaatgaca gagatcgctg cccacagtgc aagggagaga aggttgtgca ggagaagaaa     660
gtccttgaag ttattgtaga aaaggggatg cagaatgggc agaagataac attccctggc     720
gaagctgatg aagcgccgga cacaattact ggggatatcg tctttgtcct tcagcagaag     780
gaacatccca aattcaaaag aaaggctgaa gatcttttg tagagcacac tttgtcccttt     840 accgaggcct tgtgtggctt ccaatttgtg ctgactcact ggatagccg tcagcttctt     900 attaaatcaa atcccgggga agttgtgaag cctgattcat acaaggctat aaatgatgag     960
ggaatgccca tgtatcagag gccatttatg aaggggaaac tttacattca cttcactgtg    1020
gagtttccag attctctaaa ccctgatcaa gttaaggcct tggaggctgt tctgccacca    1080
aagccttctt cacaattgac agacatggag ctggatgaat gtgaggaaac tacactccat    1140
gatgtcaaca tggaggagga gactaggagg aagcagcaac aagctcagga ggcatatgat    1200
gaggatgatg acatgcctgg tggtgcacag agggtacagt gcgcccagca gtaa         1254

<210> SEQ ID NO 3
<211> LENGTH: 417
<212> TYPE: PRT
<213> ORGANISM: Artificial Sequence
<220> FEATURE:
<223> OTHER INFORMATION: Transgenic Arabidopsis thaliana
```

<220> FEATURE:
<223> OTHER INFORMATION: GmDNJ1 deduced amino acid sequence

<400> SEQUENCE: 3

```
Met Phe Gly Arg Ala Pro Lys Lys Ser Asp Asn Thr Arg Tyr Tyr Glu
  1               5                  10                  15

Ile Leu Gly Val Ser Lys Asn Ala Ser Gln Asp Asp Leu Lys Lys Ala
             20                  25                  30

Tyr Lys Lys Ala Ala Ile Lys Asn His Pro Asp Lys Gly Gly Asp Pro
         35                  40                  45

Glu Lys Phe Lys Glu Leu Ala Gln Ala Tyr Glu Val Leu Ser Asp Pro
     50                  55                  60

Glu Lys Arg Glu Ile Tyr Asp Gln Tyr Gly Glu Asp Ala Leu Lys Glu
 65                  70                  75                  80

Gly Met Gly Gly Gly Gly His Asp Pro Phe Asp Ile Phe Ser Ser
             85                  90                  95

Phe Phe Gly Gly Gly Ser Pro Phe Gly Ser Gly Ser Ser Arg Gly
                100                 105                 110

Arg Arg Gln Arg Arg Gly Glu Asp Val Val His Pro Leu Lys Val Ser
         115                 120                 125

Leu Glu Asp Leu Tyr Leu Gly Thr Ser Lys Lys Leu Ser Leu Ser Arg
    130                 135                 140

Asn Val Ile Cys Ser Lys Cys Ser Gly Lys Gly Ser Lys Ser Gly Ala
145                 150                 155                 160

Ser Met Lys Cys Ala Gly Cys Gln Gly Thr Gly Met Lys Val Ser Ile
                165                 170                 175

Arg His Leu Gly Pro Ser Met Ile Gln Gln Met Gln His Ala Cys Asn
            180                 185                 190

Glu Cys Lys Gly Thr Gly Glu Thr Ile Asn Asp Arg Asp Arg Cys Pro
        195                 200                 205

Gln Cys Lys Gly Glu Lys Val Val Gln Glu Lys Val Leu Glu Val
    210                 215                 220

Ile Val Glu Lys Gly Met Gln Asn Gly Gln Lys Ile Thr Phe Pro Gly
225                 230                 235                 240

Glu Ala Asp Glu Ala Pro Asp Thr Ile Thr Gly Asp Ile Val Phe Val
                245                 250                 255

Leu Gln Gln Lys Glu His Pro Lys Phe Lys Arg Lys Ala Glu Asp Leu
            260                 265                 270

Phe Val Glu His Thr Leu Ser Leu Thr Glu Ala Leu Cys Gly Phe Gln
        275                 280                 285

Phe Val Leu Thr His Leu Asp Ser Arg Gln Leu Leu Ile Lys Ser Asn
    290                 295                 300

Pro Gly Glu Val Val Lys Pro Asp Ser Tyr Lys Ala Ile Asn Asp Glu
305                 310                 315                 320

Gly Met Pro Met Tyr Gln Arg Pro Phe Met Lys Gly Lys Leu Tyr Ile
                325                 330                 335

His Phe Thr Val Glu Phe Pro Asp Ser Leu Asn Pro Asp Gln Val Lys
            340                 345                 350

Ala Leu Glu Ala Val Leu Pro Pro Lys Pro Ser Ser Gln Leu Thr Asp
        355                 360                 365

Met Glu Leu Asp Glu Cys Glu Glu Thr Thr Leu His Asp Val Asn Met
    370                 375                 380

Glu Glu Glu Thr Arg Arg Lys Gln Gln Gln Ala Gln Glu Ala Tyr Asp
385                 390                 395                 400
```

```
Glu Asp Asp Asp Met Pro Gly Gly Ala Gln Arg Val Gln Cys Ala Gln
                405                 410                 415

Gln

<210> SEQ ID NO 4
<211> LENGTH: 415
<212> TYPE: PRT
<213> ORGANISM: Artificial Sequence
<220> FEATURE:
<223> OTHER INFORMATION: DnaJ protein GMSMP

<400> SEQUENCE: 4

Met Phe Gly Arg Ala Pro Lys Lys Ser Asp Asn Thr Arg Tyr Tyr Glu
  1               5                  10                  15

Ile Leu Gly Val Ser Lys Asn Ala Ser Gln Asp Asp Leu Lys Lys Ala
             20                  25                  30

Tyr Ala Tyr Lys Lys Ala Ala Ile Lys Asn His Pro Asp Lys Gly Gly
         35                  40                  45

Asp Pro Glu Lys Phe Lys Glu Leu Ala Gln Ala Tyr Glu Val Leu Ser
     50                  55                  60

Asp Pro Glu Lys Arg Glu Ile Tyr Asp Gln Tyr Gly Glu Asp Ala Leu
 65                  70                  75                  80

Lys Glu Gly Met Gly Gly Gly Gly His Asp Pro Phe Asp Ile Phe
                 85                  90                  95

Ser Ser Phe Phe Gly Gly Gly Ser Pro Phe Gly Ser Gly Ser Ser
                100                 105                 110

Arg Gly Arg Arg Gln Arg Arg Gly Glu Asp Val Val His Pro Leu Lys
            115                 120                 125

Val Ser Leu Glu Asp Leu Tyr Leu Gly Thr Ser Lys Lys Leu Ser Leu
        130                 135                 140

Ser Arg Asn Val Ile Cys Ser Lys Cys Ser Gly Lys Gly Ser Lys Ser
145                 150                 155                 160

Gly Ala Ser Met Lys Cys Ala Gly Cys Gln Gly Met Lys Val Ser Ile
                165                 170                 175

Arg His Leu Gly Pro Ser Met Ile Gln Gln Met Gln His Ala Cys Asn
            180                 185                 190

Glu Cys Lys Gly Thr Gly Glu Thr Ile Asn Asp Arg Asp Arg Cys Pro
        195                 200                 205

Gln Cys Lys Gly Glu Lys Val Val Gln Glu Lys Lys Val Leu Glu Val
    210                 215                 220

Ile Val Glu Lys Gly Met Gln Asn Gly Gln Lys Ile Thr Phe Pro Gly
225                 230                 235                 240

Glu Ala Asp Glu Ala Pro Asp Thr Ile Thr Gly Asp Ile Val Phe Val
                245                 250                 255

Leu Gln Gln Lys Glu His Pro Lys Phe Lys Arg Lys Ala Glu Asp Leu
            260                 265                 270

Phe Val Glu His Thr Leu Ser Leu Thr Glu Ala Leu Cys Gly Phe Val
        275                 280                 285

Leu Thr His Leu Asp Ser Arg Gln Leu Leu Ile Lys Ser Asn Pro Gly
    290                 295                 300

Glu Val Val Lys Pro Asp Ser Tyr Lys Ala Ile Asn Asp Glu Gly Met
305                 310                 315                 320

Pro Met Tyr Gln Arg Pro Phe Met Lys Gly Lys Leu Tyr Ile His Phe
                325                 330                 335

Thr Val Glu Phe Pro Asp Ser Leu Asn Pro Asp Gln Val Lys Ala Leu
            340                 345                 350
```

```
Glu Ala Val Leu Pro Pro Lys Pro Ser Ser Gln Leu Thr Asp Met Glu
            355                 360                 365

Leu Asp Glu Cys Glu Thr Thr Leu His Asp Val Asn Met Glu Glu
370                 375                 380

Glu Thr Arg Arg Lys Gln Gln Gln Ala Gln Glu Ala Tyr Asp Glu Asp
385                 390                 395                 400

Asp Asp Met Pro Gly Gly Ala Gln Arg Val Gln Cys Ala Gln Gln
            405                 410                 415

<210> SEQ ID NO 5
<211> LENGTH: 409
<212> TYPE: PRT
<213> ORGANISM: Artificial Sequence
<220> FEATURE:
<223> OTHER INFORMATION: DnaJ protein ScP25591

<400> SEQUENCE: 5

Met Val Lys Glu Thr Lys Phe Tyr Asp Ile Leu Gly Val Pro Val Thr
1               5                   10                  15

Ala Thr Asp Val Glu Ile Lys Lys Ala Tyr Arg Lys Cys Ala Leu Lys
            20                  25                  30

Tyr His Pro Asp Lys Asn Pro Ser Glu Glu Ala Ala Glu Lys Phe Lys
        35                  40                  45

Glu Ala Ser Ala Ala Tyr Glu Ile Leu Ser Asp Pro Glu Lys Arg Asp
    50                  55                  60

Ile Tyr Asp Gln Phe Gly Glu Asp Gly Leu Ser Gly Ala Gly Gly Ala
65                  70                  75                  80

Gly Gly Phe Pro Gly Gly Gly Phe Gly Phe Asp Asp Ile Phe Ser
                85                  90                  95

Gln Phe Phe Gly Ala Gly Gly Ala Gln Arg Pro Arg Gly Pro Gln Arg
            100                 105                 110

Gly Lys Asp Ile Lys His Glu Ile Ser Ala Ser Leu Glu Glu Leu Tyr
        115                 120                 125

Lys Gly Arg Thr Ala Lys Leu Ala Leu Asn Lys Gln Ile Leu Cys Lys
130                 135                 140

Glu Cys Glu Gly Arg Gly Gly Lys Lys Gly Ala Val Lys Lys Cys Thr
145                 150                 155                 160

Ser Cys Asn Gly Gln Gly Ile Lys Phe Val Thr Arg Gln Met Gly Pro
                165                 170                 175

Met Ile Gln Arg Phe Gln Thr Glu Cys Asp Val Cys His Gly Thr Gly
            180                 185                 190

Asp Ile Ile Asp Pro Lys Asp Arg Cys Lys Ser Cys Asn Gly Lys Lys
        195                 200                 205

Val Glu Asn Glu Arg Lys Ile Leu Glu Val His Val Glu Pro Gly Met
    210                 215                 220

Lys Asp Gly Gln Arg Ile Val Phe Lys Gly Glu Ala Asp Gln Ala Pro
225                 230                 235                 240

Asp Val Ile Pro Gly Asp Val Val Phe Ile Val Ser Glu Arg Pro His
                245                 250                 255

Lys Ser Phe Lys Arg Asp Gly Asp Asp Leu Val Tyr Glu Ala Glu Ile
            260                 265                 270

Asp Leu Leu Thr Ala Ile Ala Gly Gly Glu Phe Ala Leu Glu His Val
        275                 280                 285

Ser Gly Asp Trp Leu Lys Val Gly Ile Val Pro Gly Glu Val Ile Ala
    290                 295                 300
```

```
Pro Gly Met Arg Lys Val Ile Glu Gly Lys Gly Met Pro Ile Pro Lys
305                 310                 315                 320

Tyr Gly Gly Tyr Gly Asn Leu Ile Ile Lys Phe Thr Ile Lys Phe Pro
                325                 330                 335

Glu Asn His Phe Thr Ser Glu Glu Asn Leu Lys Lys Leu Glu Glu Ile
            340                 345                 350

Leu Pro Pro Arg Ile Val Pro Ala Ile Pro Lys Lys Ala Thr Val Asp
        355                 360                 365

Glu Cys Val Leu Ala Asp Phe Asp Pro Ala Lys Tyr Asn Arg Thr Arg
    370                 375                 380

Ala Ser Arg Gly Gly Ala Asn Tyr Asp Ser Asp Glu Glu Glu Gln Gly
385                 390                 395                 400

Gly Glu Gly Val Gln Cys Ala Ser Gln
                405
```

<210> SEQ ID NO 6
<211> LENGTH: 397
<212> TYPE: PRT
<213> ORGANISM: Artificial Sequence
<220> FEATURE:
<223> OTHER INFORMATION: DnaJ protein HsP31689

<400> SEQUENCE: 6

```
Met Val Lys Glu Thr Thr Tyr Tyr Asp Val Leu Gly Val Lys Pro Asn
1               5                   10                  15

Ala Thr Gln Glu Glu Leu Lys Lys Ala Tyr Arg Lys Leu Ala Leu Lys
                20                  25                  30

Tyr His Pro Asp Lys Asn Pro Asn Glu Gly Glu Lys Phe Lys Gln Ile
            35                  40                  45

Ser Gln Ala Tyr Glu Val Leu Ser Asp Ala Lys Lys Arg Glu Leu Tyr
    50                  55                  60

Asp Lys Gly Gly Glu Gln Ala Ile Lys Glu Gly Gly Ala Gly Gly Gly
65                  70                  75                  80

Phe Gly Ser Pro Met Asp Ile Phe Asp Met Phe Gly Gly Gly Gly
                85                  90                  95

Arg Met Gln Arg Glu Arg Arg Gly Lys Asn Val Val His Gln Leu Ser
                100                 105                 110

Val Thr Leu Glu Asp Leu Tyr Asn Gly Ala Thr Arg Lys Leu Ala Leu
            115                 120                 125

Gln Lys Asn Val Ile Cys Asp Lys Cys Glu Gly Arg Gly Gly Lys Lys
    130                 135                 140

Gly Ala Val Glu Cys Cys Pro Asn Cys Arg Gly Thr Gly Met Gln Ile
145                 150                 155                 160

Arg Ile His Gln Ile Gly Pro Gly Met Val Gln Ile Gln Ser Val
                165                 170                 175

Cys Met Glu Cys Gln Gly His Gly Glu Arg Ile Ser Pro Lys Asp Arg
            180                 185                 190

Cys Lys Ser Cys Asn Gly Arg Lys Ile Val Arg Glu Lys Lys Ile Leu
    195                 200                 205

Glu Val His Ile Asp Lys Gly Met Lys Asp Gly Gln Lys Ile Thr Phe
    210                 215                 220

His Gly Glu Gly Asp Gln Glu Pro Gly Leu Glu Pro Gly Asp Ile Ile
225                 230                 235                 240

Ile Val Leu Asp Gln Lys Asp His Ala Val Phe Thr Arg Arg Gly Glu
                245                 250                 255
```

```
Asp Leu Phe Met Cys Met Asp Ile Gln Leu Val Glu Ala Leu Cys Gly
                260                 265                 270

Phe Gln Lys Pro Ile Ser Thr Leu Asp Asn Arg Thr Ile Val Ile Thr
            275                 280                 285

Ser His Pro Gly Gln Ile Val Lys His Gly Asp Ile Lys Cys Val Leu
        290                 295                 300

Asn Glu Gly Met Pro Ile Tyr Arg Arg Pro Tyr Glu Lys Gly Arg Leu
305                 310                 315                 320

Ile Ile Glu Phe Lys Val Asn Phe Pro Glu Asn Gly Phe Leu Ser Pro
                325                 330                 335

Asp Lys Leu Ser Leu Leu Glu Lys Leu Leu Pro Glu Arg Lys Glu Val
            340                 345                 350

Glu Glu Thr Asp Glu Met Asp Gln Val Glu Leu Val Asp Phe Asp Pro
        355                 360                 365

Asn Gln Glu Arg Arg Arg His Tyr Asn Gly Glu Ala Tyr Glu Asp Asp
370                 375                 380

Glu His His Pro Arg Gly Gly Val Gln Cys Gln Thr Ser
385                 390                 395
```

<210> SEQ ID NO 7
<211> LENGTH: 415
<212> TYPE: PRT
<213> ORGANISM: Artificial Sequence
<220> FEATURE:
<223> OTHER INFORMATION: DnaJ protein HbAAD12055

<400> SEQUENCE: 7

```
Met Phe Gly Arg Ala Pro Lys Lys Ser Asp Asn Thr Lys Tyr Tyr Glu
1               5                   10                  15

Ile Leu Gly Val Ser Lys Asn Ala Ser Gln Asp Asp Leu Lys Lys Ala
                20                  25                  30

Tyr Arg Lys Ala Ala Ile Lys Asn His Pro Asp Lys Gly Gly Asp Pro
            35                  40                  45

Glu Lys Phe Lys Glu Leu Ala Gln Ala Tyr Glu Val Leu Ser Asp Pro
        50                  55                  60

Glu Lys Arg Glu Ile Tyr Asp Gln Tyr Gly Glu Asp Ala Leu Lys Glu
65                  70                  75                  80

Gly Met Gly Ser Gly Gly Ala His Asp Pro Phe Asp Ile Phe Gln
                85                  90                  95

Ser Phe Phe Gly Gly Asn Pro Phe Gly Gly Gly Ser Ser Arg Gly
            100                 105                 110

Arg Arg Lys Glu Gly Glu Asp Val Ile His Pro Leu Lys Val Ser Leu
        115                 120                 125

Glu Asp Leu Tyr Asn Gly Thr Ser Lys Lys Leu Ser Leu Ser Arg Asn
130                 135                 140

Val Ile Cys Ser Lys Cys Lys Gly Lys Gly Ser Gly Ser Lys Ser Gly
145                 150                 155                 160

Ala Ser Met Lys Cys Ser Gly Cys Gln Gly Ser Gly Met Lys Val Ser
                165                 170                 175

Ile Arg Gln Leu Gly Pro Ser Met Ile Gln Gln Met Gln His Pro Cys
            180                 185                 190

Asn Glu Cys Lys Gly Thr Gly Glu Thr Ile Asn Asp Lys Asp Arg Cys
        195                 200                 205

Pro Gln Cys Lys Gly Glu Lys Val Val Gln Glu Lys Lys Val Leu Glu
210                 215                 220
```

```
Leu Ile Val Glu Lys Phe Met Gln Asn Arg Ile Thr Phe Pro Gly Glu
225                 230                 235                 240

Ala Asp Glu Ala Pro Asp Thr Ile Thr Gly Asp Ile Val Phe Val Leu
                245                 250                 255

Gln Gln Lys Glu His Pro Lys Phe Lys Arg Lys Gly Asp Asp Leu Ile
            260                 265                 270

Val Asp His Thr Leu Ser Leu Thr Glu Ala Leu Cys Ala Ser Gln Phe
        275                 280                 285

Ile Leu Tyr His Leu Asp Gly Asp Leu Leu Ile Lys Ser Gln Pro Gly
    290                 295                 300

Glu Val Val Lys Pro Asp Gln Phe Lys Ala Ile Asn Asp Glu Gly Met
305                 310                 315                 320

Pro Met Tyr Gln Arg Pro Phe Met Arg Gly Lys Leu Tyr Ile His Phe
                325                 330                 335

Ser Val Asp Phe Pro Asp Ser Leu Pro Pro Asp Gln Cys Lys Ala Leu
            340                 345                 350

Glu Ala Val Leu Pro Ser Arg Thr Ser Val Gln Leu Ser Asp Met Glu
        355                 360                 365

Leu Asp Glu Cys Glu Gly Thr Thr Leu His Asp Val Asn Phe Asp Glu
370                 375                 380

Glu Met Arg Arg Lys Gln Gln Ala Gln Glu Ala Tyr Asp Glu Asp
385                 390                 395                 400

Asp Asp Met His Gly Gly Gly Gln Arg Val Gln Cys Ala Gln Gln
                405                 410                 415

<210> SEQ ID NO 8
<211> LENGTH: 416
<212> TYPE: PRT
<213> ORGANISM: Artificial Sequence
<220> FEATURE:
<223> OTHER INFORMATION: DnaJ protein SgBAA35121

<400> SEQUENCE: 8

Met Phe Gly Arg Ala Pro Lys Lys Ser Asp Asn Thr Lys Tyr Tyr Glu
1               5                   10                  15

Val Leu Gly Val Ser Lys Ser Ala Ser Gln Asp Asp Leu Lys Lys Ala
            20                  25                  30

Tyr Arg Lys Ala Ala Ile Lys Asn His Pro Asp Lys Gly Gly Asp Pro
        35                  40                  45

Glu Lys Phe Lys Glu Leu Ala Gln Ala Tyr Glu Val Leu Ser Asp Pro
    50                  55                  60

Glu Lys Arg Glu Ile Tyr Gly Gln Tyr Gly Glu Asp Ala Leu Lys Glu
65                  70                  75                  80

Gly Met Gly Ser Gly Gly Ser Gly Ala His Asp Pro Phe Asp Ile Phe
                85                  90                  95

Gln Ser Phe Phe Gly Gly Asn Pro Phe Gly Gly Gly Gly Ser Ser
            100                 105                 110

Arg Gly Arg Arg Gln Arg Arg Gly Glu Asp Val Ile His Pro Leu Lys
        115                 120                 125

Val Ser Phe Glu Asp Leu Tyr Asn Gly Thr Ser Lys Lys Leu Ser Leu
    130                 135                 140

Ser Arg Asn Val Ile Cys Ser Lys Cys Lys Gly Lys Gly Ala Ser Ser
145                 150                 155                 160

Lys Cys Ala Gly Cys Gln Gly Ser Gly Met Lys Val Ser Ile Arg His
                165                 170                 175
```

-continued

```
Leu Gly Pro Ser Met Ile Gln Gln Met Gln His Ala Cys Asn Glu Cys
            180                 185                 190

Lys Gly Thr Gly Glu Thr Ile Asn Asp Lys Asp Arg Cys Pro Gln Cys
        195                 200                 205

Lys Gly Glu Lys Val Val Gln Glu Lys Lys Val Leu Glu Val Val Val
    210                 215                 220

Glu Lys Gly Met Gln Asn Gly Gln Lys Val Thr Phe Pro Gly Glu Ala
225                 230                 235                 240

Asp Glu Ala Pro Asp Thr Val Thr Gly Asp Ile Val Phe Val Leu Gln
                245                 250                 255

Gln Lys Asp His Pro Lys Phe Lys Arg Lys Gly Asp Asp Leu Phe Val
            260                 265                 270

Glu His Thr Leu Ser Leu Thr Glu Ala Leu Cys Gly Phe Gln Phe Val
            275                 280                 285

Leu Thr His Leu Asp Gly Arg Gln Leu Leu Ile Lys Ser Gln Pro Gly
        290                 295                 300

Glu Val Val Lys Pro Asp Gln Phe Lys Ala Ile Asn Asp Glu Gly Met
305                 310                 315                 320

Pro Met Tyr Gln Arg Pro Phe Met Arg Gly Lys Leu Tyr Ile His Phe
                325                 330                 335

Ser Val Glu Phe Pro Asp Ser Leu Ser Pro Asp Met Cys Lys Ala Leu
            340                 345                 350

Glu Ala Val Leu Pro Pro Arg Ala Ser Val Gln Leu Thr Asp Met Glu
        355                 360                 365

Leu Asp Glu Cys Glu Glu Thr Thr Leu His Asp Val Asn Ile Asp Glu
    370                 375                 380

Glu Met Arg Arg Lys Gln Gln Gln Gln Ala Gln Glu Ala Tyr Asp Glu
385                 390                 395                 400

Asp Asp Glu Met Pro Gly Gly Ala Gln Arg Val Gln Cys Ala Gln Gln
                405                 410                 415
```

ABIOTIC STRESS TOLERANCE CONFERRED BY J-DOMAIN CONTAINING PROTEINS

CROSS-REFERENCE TO RELATED APPLICATIONS

This application claims priority from U.S. Ser. No. 60/843,943 filed 11 Sep. 2006. The contents of this document are incorporated herein by reference.

REFERENCE TO SEQUENCE LISTING SUBMITTED VIA EFS-WEB

The entire content of the following electronic submission of the Sequence Listing via the USPTO EFS-WEB server, as authorized and set forth in MPEP §1730 II.B.2(a)(C), is incorporated herein by reference in its entirety for all purposes. The Sequence Listing is identified on the electronically filed .txt file as follows:

| File Name | Date of Creation | Size (bytes) |
|---|---|---|
| 549072000400Seqlist.txt | Nov. 20, 2007 | 23,509 bytes |

TECHNICAL FIELD

The invention relates to methods to confer tolerance to abiotic stress conditions, such as salinity, osmotic, and dehydration stress by enhanced expression of proteins with J-domains, in particular, DnaJ-type proteins.

BACKGROUND ART

Seed maturation proteins, or late embryogenesis abundant (LEA) proteins, are produced in abundance during the late drying phase of seed development. Most LEA proteins accumulate in seeds or vegetative tissues that were exposed to exogenous abscisic acid or that undergo abiotic stress caused by salinity or dehydration. Some LEA proteins confer salt and dehydration tolerance in transgenic plants, probably by hydrating macromolecules, sequestering ions and renaturing unfolded proteins.

Using suppression subtractive techniques, nine genes were found to be more highly expressed under abiotic stress conditions than under normal conditions. One of them (GmDNJ1) shared 99% nucleotide sequence homology to *Glycine max* seed maturation protein PM37 (GmPM37) deposited in GenBank as AF 169022, which is a DnaJ homolog. As shown in FIG. 11a, it contains the characteristic components of DnaJ including the conserved N-terminal J-domain, a glycine/phenylalanine rich domain, a domain that includes a (CXXCXGXG)$_4$ (SEQ ID NO:1) zinc finger type motif and an uncharacterized C-terminal domain. (Cyr, D. M., et al., *J. Biol. Chem.* (1994) 269:9798-9804, Hennessy, F., et al., *Cell Stress & Chaperones* (2000) 4:347-358). GmDNJ1 did not resemble any LEA proteins.

DnaJ-like proteins are believed to serve as chaperone or co-chaperone proteins principally by aiding the chaperone function of Hsp70s. Hsp70 is one of many heat shock proteins originally found to occur in *Drosophila* larvae in response to elevated temperatures. Heat shock proteins in general, while they may be produced either constitutively or under stress conditions, are believed, to play a chaperone role.

DnaJ-like proteins are defined by a conserved "J" region of approximately 73 amino acids (based on the originally disclosed *E. coli* protein, typically occurring toward the N-terminus of the protein (Hennessy, F., et al., supra). This domain is slightly shorter in the eucaryotic counterparts. As noted by Hennessy, et al., DnaJ-like proteins have been classified as: Type I which contain similarity to DnaJ over all domains, including the J-domain, the glycine-phenylalanine rich domain, and the (CXXCXGXG)$_4$ (SEQ ID NO:1) motif; Type II which contain the J-domain and the glycine-phenylalanine rich region; and Type III which contain only the J-domain. These groups have been renamed A, B and C, respectively.

The J-domain is required to include the triplet histidine-proline-aspartic (HPD) and also contains a number of other highly conserved regions. Hennessy, et al., (supra) in FIG. 3 provides detailed comparison of the J-domains of a number of DnaJ-like proteins indicating greater consensus in these regions among proteins of Types I and II than of Type III.

Miernyk, J. A., *Cell Stress & Chaperones* (2001) 6:209-218 using analysis of the genome and EST profiles of *Arabidopsis thaliana* shows that the genome encodes 89 J-domain containing proteins which correspond to varying levels of EST's. Of these, only one appears to be highly expressed; it is a Type III DnaJ-like protein. No analysis of actual protein levels was performed.

DnaJ expression has been reported to be associated with salt and dehydration tolerance in plants. Zhu, et al, *Cell* (1993) 5:341-349 showed that the expression of a DnaJ homologue from the higher plant *Atriplex nummularia* (ANJ1) was induced in plant cell culture under salinity stress. Recently, Nguyuen, et al., *Mol. Gen. Genomics* (2004) 272:35-46 developed a marker for mapping of quantitative trait loci (QTL) regions for dehydration tolerance in rice, which was shown to be similar to *Zea mays* DnaJ-related protein (ZMDJ1), which was induced by heat stress (Baszczynski, et al., *Maydica* (1997) 42:189-201). Although these studies reported the induction of DnaJ homologue under salt and dehydration stresses, no characterization of the effect of ANJ1 and ZMDJ1 on salt or dehydration tolerance was reported.

A group of seed maturation proteins includes small heat shock proteins (sHsps), but does not include DnaJ or Hsp40 (Wise, *BMC Bioinformatics* (2003) 29:52-70). Only GmPM37 (GmDNJ1) has been reported as a DnaJ-like seed maturation protein. The deduced protein sequence showed that GmDNJ1 contains the conserved motifs of DnaJ, and has a predicted molecular weight similar to common DnaJ proteins (Hdj1: 38 kDa; Ydj1: 45 kDa; Hsp40: 41 kDa).

The present applicants are not aware of any reports describing the functional role of DnaJ proteins in conferring tolerance in plants to abiotic stress except heat shock.

DISCLOSURE OF THE INVENTION

The invention provides methods to confer tolerance on higher plants against salinity, osmotic, and dehydration stress by employing expression systems for proteins that contain J-domain consensus sequences and preferably also contain glycine/phenylalanine domain and (CXXCXGXG)$_4$ (SEQ ID NO:1) sequences characteristic of DnaJ proteins.

Thus, in one aspect, the invention is directed to a method to protect plants or plant cells from salinity, osmotic, and dehydration stress which method comprises modifying said plants or plant cells to produce a heterologous protein that contains a conserved DnaJ J-domain.

In another aspect, the invention provides a method to protect plants or plant cells from salinity, osmotic, and dehydration stress by modifying the plants or plant cells by coupling an endogenous nucleotide sequence encoding a protein that comprises a DnaJ J-domain to a promoter heterologous to said sequence operable in plants which is either also heterologous to the plants or plant cells or is a high expression promoter endogenous to said plant.

The ability of the methods of the invention to confer tolerance to salinity, osmotic, and dehydration stress is particularly helpful when combined with water-saving techniques in the culturing of plants that have been modified to be tolerant. Thus, it is possible to combine the methods of the invention with reduced irrigation or other methods to reduce water use in the culture of crops.

In still another aspect, the invention is directed to nucleic acid constructs for carrying out the foregoing methods. These constructs include nucleic acid transformation vectors which comprise a nucleotide sequence encoding a protein that comprises a DnaJ-J-domain operably linked to a promoter operable in plant cells. Such constructs also include transformation vectors which comprise sequences for homologous recombination or other means of insertion of a high expression level promoter into the genome of plants or plant cells.

In still other aspects, the invention includes transgenic plants and plant cells that have been modified as described above.

In still another aspect, the invention is directed to a method to identify successful transformants by enhanced expression of a protein that comprises a DnaJ-J-domain as a selection marker.

BRIEF DESCRIPTION OF THE DRAWINGS

FIGS. 1a-1d show Northern blot analyses designed to detect mRNA encoding GmDNJ1 under salinity stress in salt tolerant (Wenfeng7) and salt sensitive (Union) soybean cultivars. FIG. 1a shows Northern blots of Union leaf. FIG. 1b shows Northern blots of Wenfeng7 leaf. FIG. 1c shows Northern blots of Union root. FIG. 1d shows Northern blots of Wenfeng7 root: CK: control without treatment; T0.3: 0.3% NaCl; T0.6: 0.6% NaCl; T0.9: 0.9% NaCl. T1.2: 1.2% NaCl.

FIG. 2a shows a Northern blot analysis of expression levels of GmDNJ1 at various times after flowering; FIG. 2b shows the appearance of pods at these time periods: The results of Northern blots (a) and typical appearance of the pod during seed maturation (b) were shown.

FIG. 3 shows Northern blots of GmDNJ1 expression in four *Arabidopsis* transgenic lines in comparison to controls: Col-0: wild type; V7: transformant with empty vector; A-3-4, M-3-1, D-3-2 and P-3-6: GmDNJ1 transgenic lines.

FIGS. 4a and 4b show the effects of osmotic stress (FIG. 4a) and salinity stress (FIG. 4b) on the phenotypes of wild type and transgenic *Arabidopsis* lines expressing the *Arabidopsis* ASN1 cDNA (as negative transgenic control) or GmDNJ1.

FIG. 5 is a graph that shows the effects of salinity and osmotic stresses on the fresh weight of wild type and transgenic *Arabidopsis* lines expressing the *Arabidopsis* ASN1 cDNA (as negative transgenic control) or GmDNJ1: Col-0: wild type; ASN1: transgenic line expressing the *Arabidopsis* ASN1 cDNA (as a negative transgenic control); A-3-4, M-3-1: transgenic lines expressing GmDNJ1.

FIG. 6 shows Northern blots of GmDNJ1 in rice transgenic lines WT: wild type; other numbers: GmDNJ1 transgenic lines.

FIGS. 7a and 7b are photographs which contrast the response to salinity stress of GmDNJ1 transgenic lines (segregating population) and wild type rice.

FIGS. 8a and 8b show the effects of dehydration stress (FIG. 8a) and salinity stress (FIG. 8b) on the phenotypes of the untransformed wild type and transgenic rice lines expressing the *G. max* AS2 cDNA (as negative transgenic control) or GmDNJ1: water was removed and then replenished (a) and salinity stress (200 mM NaCl) (b). WT: wild type; AS2: AS2 transgenic lines; other numbers: GmDNJ1 transgenic lines.

FIGS. 9a and 9b show the effects of dehydration stress and salinity stress on the survival rate of wild type and transgenic rice lines expressing the *G. max* AS2 cDNA (as negative transgenic control) or GmDNJ1: water was removed and then replenished (a) and salinity stress (200 mM NaCl) (b). WT: wild type; AS2: AS2 transgenic lines; other numbers: GmDNJ1 transgenic lines. N=12.

FIGS. 10a and 10b show the effects of dehydration stress and salinity stress on the fresh weight of wild type and transgenic rice lines expressing the *G. max* AS2 cDNA (as negative transgenic control) or GmDNJ1: water was removed and then replenished (a) and salinity stress (200 mM NaCl) (b). WT: wild type; AS2: AS2 transgenic lines; other numbers: GmDNJ1 transgenic lines. N=12.

FIGS. 11a and 11b show a comparison of the amino acid sequence of GmDNJ1 protein to known DnaJ proteins (FIG. 11a) (SEQ ID NOS:4-8) and the co-chaperone activity of purified GmDNJ1 (FIG. 11b) in form of GST-GmDNJ1 fusion proteins produced in *E. coli* cells: Mean values and standard errors of at least three determinations are shown. Luciferase activity in the presence of the *Escherichia coli* homologous system (lane 3) is set to 100%.

MODES OF CARRYING OUT THE INVENTION

It has been found that proteins comprising a DnaJ conserved J-domain motif are successful in conferring tolerance in plant cells and plants with respect to the stress factors of salinity, low osmotic potential, and dehydration. Plants and plant cells can exhibit this tolerance by virtue of transgenic modification to include expression systems which result in the production of such proteins. This is illustrated below in rice and in *Arabidopsis* plants, but is by no means limited to these examples. Any higher plant or cell of a higher plant is a suitable subject for the methods and materials of the present invention.

Salinity stress means that the growth substratum (including but not limited to soil and hydroponic systems) contains level of salts (including but not limited to NaCl, NaHCO$_3$, Na$_2$CO$_3$, Na$_2$SO$_4$) that limit the growth of target plants. Osmotic stress means that the growth substratum contains substances (including but not limited salts) that will decrease water potential in the growth substratum. Dehydration stress means that the growth substratum contains water less than that required for optimal growth of target plants.

In order to provide the requisite protein, plant cells are modified to contain nucleotide sequences encoding the relevant protein, optionally operably linked to control sequences operable in plants, or integrated into the genome so as to be expressed under the control of endogenous control sequences. Nucleic acid constructs may contain control sequences operable in plants operably linked to the J-domain protein-encoding sequence, which control sequences can be selected to result in constitutive, tissue-specific or non-tissue-specific, or inducible expression. A wide variety of such control sequences is available in the art, and appropriate vectors for genetic modification are also well known and, indeed, commercially available. Similarly, techniques for effecting genetic modification of plant cells and reconstituting intact plants are now well known in the art. A useful summary of the state of the art in this respect, including a reasonably comprehensive list of the types of plants and plant cells that can form the subjects of the present invention is found in U.S. Patent Publication 2004/0009476, published 14 Jan. 2004, incorporated herein by reference with respect to its disclosure of appropriate techniques for genetic manipulation of plants and the range of plants and plant cells to which these techniques may be applied.

Further, because the modified cells and plants of the invention are tolerant to stress caused by dehydration and/or high salinity stress, an expression system comprising a nucleotide sequence encoding the J-domain containing protein operably linked to control sequences operable in plants can be used as a selectable marker for successful transformation of cells. Successful transformants are more highly resistant and survive an applied stress for which the marker confers tolerance. Hence, successful transformants can be identified by virtue of their ability to survive such stress conditions.

As will be apparent from the discussion in the background section above, a protein whose expression is able to effect tolerance against salinity, osmotic, and dehydration stress must, at a minimum, contain a DnaJ-type J-domain. This domain is of approximately 60 amino acids, and is homologous to the conserved J-domains of type I (or A) DnaJ-like proteins. For purposes of definiteness, the degree of homology required is at least 80%, or 85% or 90% or 95% to that of the amino acid sequence at positions 13-77 of soybean GmDNJ1 as shown in FIG. 11a and must contain the sequence histidine-proline-aspartic (HPD). (As apparent from FIG. 11a, if GmDNJ1 were numbered independently, this region would be positions 12-77.)

In one embodiment, the protein, in addition to the DnaJ-type J-conserved domain also contains a glycine/phenylalanine rich sequence similar to that characterizing DnaJ-type I(A) proteins and/or a $(CXXCXGXG)_4$ (SEQ ID NO:1) domain also characteristic of type I(A) DnaJ proteins.

In order to effect production of the desired DnaJ-like protein in plants or plant cells, these cells or plants may be modified using a recombinant expression vector containing a heterologous nucleic acid sequence that encodes the DnaJ-type protein or may be modified by providing enhanced expression of an endogenous DnaJ-type J-domain containing protein-encoding gene. Such enhancement may be obtained by placing the nucleotide sequence representing the endogenous coding sequence on a vector wherein said coding sequence is in operable linkage with control sequences heterologous to said coding sequence which are able to effect high levels of expression of sequences under their control in plants or plant cells. Alternatively, the plants or plant cells may be modified to contain a transformation vector which comprises such powerful control sequences as well as additional nucleotide sequences that effect insertion of the control sequences into an operable linkage with an endogenous coding sequence for the desired DnaJ-like protein contained in the plant. Such sequences include, for example, sequences homologous to the endogenous DNA proximal to the coding sequence. The Cre-lox system may also be used. It will be apparent to those of ordinary skill that there are a variety of methods whereby the expression levels of the desired protein comprising at least a DnaJ-type J-domain may be obtained.

The ability of the methods of the invention to confer tolerance to salinity, osmotic, and dehydration stress is particularly helpful when combined with water-saving techniques in the culturing of plants that have been modified to be tolerant. Thus, it is possible to combine the methods of the invention with reduced irrigation or other methods to reduce water use in the culture of crops.

The following examples and results confirm and illustrate the success of the methods and constructs of the invention. In the following examples, data were analyzed using the SPSS (ver. 12.0) statistical package. Samples exhibiting significant differences ($p<0.01$ or $p<0.05$) were indicated.

EXAMPLE 1

Expression of GmDNJ1 in Response to Salinity and Dehydration Stress

In this example, expression of GmDNJ1 in leaf and root of two soybean cultivars was studied in response to salinity stress. Two soybean germplasms, Wenfeng7 (salt-tolerant) and Union (salt-sensitive), were irrigated with modified Hoagland's solution (4.5 mM $KNO_3$, 3.6 mM $Ca(NO_3)_2$, 1.2 mM $NH_4NO_3$, 3.0 mM $MgSO_4$, 1.2 mM $(NH_4)_2SO_4$, 0.25 mM $KH_2PO_4$, 4.5 µM $MnSO_4$, 4.5 µM $ZnSO_4$, 1.5 µM $CuSO_4$, 0.4 µM $(NH_4)_6Mo_7O_{24}$, 0.09 mM Fe-EDTA, and 1.5 µM $H_3BO_3$) and treated with 125 mM NaCl. Leaf and root samples were collected from 0 to 144 hours after treatment.

Northern blot analysis was performed on extracts of roots and leaves as previously described (Sambrook, J., et al., *Molecular Cloning: A Laboratory Manual*, Ed 3rd., Cold Spring Harbor Laboratory Press, New York, N.Y. (2001)). Antisense single-stranded DNA probes were labeled with digoxigenin (DIG) (Roche, Mannheim, Germany) (Finckh, U., et al., *Biotechniques* (1991) 10:35-38).

The results are shown in FIGS. 1a-1d. The lanes represented by CK represent control without treatment, T0.3 represents 0.3% NaCl, T0.6 represents treatment with 0.6% NaCl, T0.9 represents treatment with 0.9% NaCl and T1.2 represents treatment with 1.2% NaCl. Salinity stress led to an increase in the steady-state mRNA levels of GmDNJ1 in leaf of both cultivars, more dramatically shown in Union, confirming that the GmDNJ1 gene expression was induced by salinity stress. For Wenfeng7, the expression of GmDNJ1 in leaf was also induced, though to a lesser extent. The expression of GmDNJ1 in Wenfeng7 leaf generally under non-stress conditions was higher than that in Union. Results for roots are shown in FIGS. 1c and 1d and are similar to those for leaf.

Correlation with seed maturation and inhibition was also studied, again, using extracts and analyzing by Northern blot. For seed maturation, 1,300 Union individuals were grown in soil supplemented with modified Hoagland's solution in an environment-controlled greenhouse. About 1,500 flowers were tagged at the first day after flowering by using different color thread. Soybean pods were collected at $17^{th}$, $22^{nd}$, $27^{th}$, $32^{nd}$, $37^{th}$, $42^{nd}$, $47^{th}$ and $52^{nd}$ days after flowering.

The results are shown in FIG. 2. The Northern blot analysis shows that GmDNJ1 expression was induced from 17-37 days after flowering and then decreases slightly, as shown in FIG. 2a. FIG. 2b shows the general appearance of the pods after flowering.

EXAMPLE 2

Transgenic *Arabidopsis thaliana*

The GmDNJ1 encoding sequence (SEQ ID NO:2) and deduced amino acid sequence (SEQ ID NO:3) are as follows:

```
GmDNJ1 sequence
   1    ATGTTTGGGA GGGCACCGAA GAAGAGCGAT AATACGAGGT ACTACGAAAT

51    CCTCGGCGTC TCCAAGAACG CTTCGCAGGA TGATCTGAAG AAGGCTTACA

101    AGAAAGCCGC CATTAAGAAT CACCCCGACA AGGGCGGTGA TCCCGAGAAG

151    TTTAAAGAGC TGGCGCAAGC TTATGAGGTT CTGAGTGACC CTGAGAAGCG

201    TGAGATATAT GATCAGTATG GTGAAGATGC GCTTAAGGAA GGAATGGGTG

251    GTGGCGGTGG CCATGATCCA TTTGATATCT TTTCATCTTT CTTTGGCGGT

301    GGGAGTCCCT TTGGATCAGG TGGAAGTAGT CGAGGTAGGA GGCAGAGGCG

351    CGGAGAAGAC GTGGTTCACC CTCTCAAGGT CTCTTTGGAG GACCTTTATC

401    TTGGAACTTC CAAGAAGCTC TCCCTCTCCA GAAATGTTAT ATGCTCCAAG

451    TGCAGTGGCA AGGGTTCTAA GTCTGGTGCT TCGATGAAGT GTGCTGCTTG

501    TCAAGGAACT GGTATGAAGG TTTCTATAAG ACATCTTGGC CCATCCATGA

551    TTCAGCAAAT GCAGCATGCC TGCAATGAAT GTAAGGGTAC TGGAGAAACT

601    ATCAATGACA GAGATCGCTG CCCACAGTGC AAGGGAGAGA AGGTTGTGCA

651    GGAGAAGAAA GTCCTTGAAG TTATTGTAGA AAAGGGGATG CAGAATGGGC

701    AGAAGATAAC ATTCCCTGGC GAAGCTGATG AAGCGCCGGA CACAATTACT

751    GGGGATATCG TCTTTGTCCT TCAGCAGAAG GAACATCCCA AATTCAAAAG

801    AAAGGCTGAA GATCTTTTTG TAGAGCACAC TTTGTCCCTT ACCGAGGCCT

851    TGTGTGGCTT CCAATTTGTG CTGACTCACT TGGATAGCCG TCAGCTTCTT

901    ATTAAATCAA ATCCCGGGGA AGTTGTGAAG CCTGATTCAT ACAAGGCTAT

951    AAATGATGAG GGAATGCCCA TGTATCAGAG GCCATTTATG AAGGGGAAAC

1001    TTTACATTCA CTTCACTGTG GAGTTTCCAG ATTCTCTAAA CCCTGATCAA

1051    GTTAAGGCCT TGGAGGCTGT TCTGCCACCA AAGCCTTCTT CACAATTGAC

1101    AGACATGGAG CTGGATGAAT GTGAGGAAAC TACACTCCAT GATGTCAACA

1151    TGGAGGAGGA GACTAGGAGG AAGCAGCAAC AAGCTCAGGA GGCATATGAT

1201    GAGGATGATG ACATGCCTGG TGGTGCACAG AGGGTACAGT GCGCCCAGCA

1251    GTAA
```

MFGRAPKKSDNTRYYEILGVSKNASQDDLKKAYKKAAIKNHPDKGGDPEKFKELAQAYEV

LSDPEKREIYDQYGEDALKEGMGGGGGHDPFDIFSSFFGGGSPFGSGGSSRGRRQRRGED

VVHPLKVSLEDLYLGTSKKLSLSRNVICSKCSGKGSKSGASMKCAGCQGTGMKVSIRHLG

PSMIQQMQHACNECKGTGETINDRDRCPQCKGEKVVQEKKVLEVIVEKGMQNGQKITFPG

EADEAPDTITGDIVFVLQQKEHPKFKRKAEDLFVEHTLSLTEALCGFQFVLTHLDSRQLL

IKSNPGEVVKPDSYKAINDEGMPMYQRPFMKGKLYIHFTVEFPDSLNPDQVKALEAVLPP

KPSSQLTDMELDECEETTLHDVNMEEETRRKQQQAQEAYDEDDDMPGGAQRVQCAQQ-

A recombinant nucleic acid containing GmDNJ1 under the control of the constitutive Cauliflower Mosaic Virus 35S promoter was cloned into a binary vector (Brears, T., et al., *Plant Physiol.* (1993) 103:1285-1290), introduced into *Agrobacterium*, and transformed into *A. thaliana* using a vacuum infiltration protocol (Bechtold, N., et al., *Arabidopsis Protocols*, Humana Press Inc., Totowa N.J., (1993) 259-266). After selecting the transformants on antibiotic-containing media, successful integration of the transgene into the genome was verified by PCR screening using gene specific primers; Northern blot analysis was performed to confirm the expression of the transgene in the transgenic plant lines. Seeds of $T_3$ homozygous lines with single insert were obtained and used in subsequent physiological studies. Four GmDNJ1 homozygous transgenic lines of *Arabidopsis thaliana* were constructed. A-3-4 and M-3-1, which had comparatively high expression of GmDNJ1, were chosen for functional analysis. FIG. 3 shows comparative expression levels in the four transformants compared to untransformed control (Col-0) and a transformant with empty vector (V7), where, in both, expression is undetectable.

EXAMPLE 3

Stress Tolerance of Transgenic *A. thaliana*

The effects of osmotic and salinity stresses on the vegetative growth of *A. thaliana* were studied in this example.

The wild type Col-0, the ASN1 transgenic line (a transgenic *A. thaliana* expressing the ASN1 clone (Lam, et al, *Plant Physiol* (2003) 132:926-935) using the same vector as the GmDNJ1 constructs), and two GmDNJ1 transgenic lines (A-3-4 and M-3-1) were germinated on MS agar plates for 14 days and then transferred to sand culture. Plants were grown for 12 days in sand culture and irrigated with ⅛ MS medium, followed by the addition of 15% PEG or 500 mM NaCl (in ⅛ MS medium) for 6 days, in a growth chamber kept at about 22° C. with a 16 h light (intensity about 130 µE)-8 h dark cycle.

Treatment with 15% PEG (osmotic stress) significantly retarded the growth of Col-0 and the ASN1 transgenic line while the GmDNJ1 transgenic lines could grow much better (FIGS. 4*a* and 5).

In the same experiment as above, treatment with 15% PEG (osmotic stress) significantly reduced the fresh weight of Col-0 and the ASN1 transgenic line while the GmDNJ1 transgenic lines could grow much better (FIGS. 4*b* and 5).

EXAMPLE 4

Transgenic *Oryza sativa*

GmDNJ1 was cloned into a double T-DNA plasmid, pSB130 (from Dr. Qiaoquan Liu and Prof. Samuel Sun at the Chinese University of Hong Kong). This plasmid has two T-DNA, one harboring the hygromycin resistance gene (selectable marker) and the other possessing a multiple cloning site for target gene cloning. The construct was introduced into the parent rice line Nipponbare via *Agrobacteria*-mediated transformation methods. GmDNJ1 homozygous transgenic lines of rice were constructed. FIG. 6 shows expression levels of GmDNJ1 in five independent transgenic rice lines whereas in the parent Nipponbare, the expression is undetectable.

EXAMPLE 5

Stress Tolerance of Transgenic *Oryza sativa*

The effects of osmotic and salinity stresses on the vegetative growth of rice (*Oryza sativa*) was studied in this example.

After germination in the dark for 10 days, triplicate sets each containing the wild type parent, the AS2 transgenic line (a transgenic *O. sativa* expressing the AS2 clone using the same vector as the GmDNJ1 constructs) and five independent GmDNJ1 transgenic rice lines were grown in ½ MS liquid medium for another 9 days, in a growth chamber kept at about 28° C. with a 16 h light (intensity about 120 µE)-8 h dark cycle. The first group was treated with ½ MS liquid medium supplemented with 200 mM NaCl for 2 days followed by irrigation of ½ MS liquid medium for 2 days. Dehydration stress was introduced to another group by the removal of the liquid growth medium for 16 hours followed by replenishment of ½ MS liquid medium for 3 days. The control group was irrigated with ½ MS liquid medium throughout the whole testing period.

Removal of liquid growth medium (dehydration stress) led to the initial rolling-up of leaves in both wild type and transgenic rice. Replenishment of ½ MS liquid medium could rescue the GmDNJ1 transgenic lines but not the untransformed parent and the AS2 transgenic line (FIG. 8*a*). The recovery rates of GmDNJ1 transgenic lines under this treatment were significantly higher than that of the untransformed parent and the AS2 transgenic line (FIG. 9*a*). The resulting fresh weights of GmDNJ1 transgenic lines under this treatment were also significantly higher than that of the untransformed parent and the AS2 transgenic line (FIG. 10*a*).

Treatment of 200 mM NaCl (salinity stress) led to drooping of leaves and salt damage symptoms in both wild type and transgenic rice. Recovery in ½ MS liquid medium could rescue the GmDNJ1 transgenic lines but not the untransformed parent and the AS2 transgenic line (FIG. 8*b*). The recovery rates of GmDNJ1 transgenic lines under this treatment were significantly higher than that of the untransformed parent and the AS2 transgenic line (FIG. 9*b*). The resulting fresh weights of GmDNJ1 transgenic lines under this treatment were significantly higher than that of the untransformed parent and the AS2 transgenic line (FIG. 10*b*).

The GmDNJ1 transgenic lines and the untransformed plant were also grown in the experimental field with high salt content. Some individual plants in the transgenic lines (segregating populations) survived while the untransformed plant all wilted and died (FIG. 7).

EXAMPLE 6

Co-Chaperone Activity of the GmDNJ1 Protein

Co-chaperone activity assay was performed by monitoring the activity of heat-denatured luciferase (Zmijewski, et al., *J. Mol. Biol.* (2004) 336:539-549).

The GmDNJ1 cDNA sequence was cloned into the expression vector pGEX-4T-1 (GE Healthcare) to form a chimeric construct, to produce Glutathione S-transferase (GST)-GmDNJ1 fusion protein in *E. coli* cells (bacterial strain used: BL23 (DE3)).

Firefly luciferase (Promega) was incubated for 10 min at 25° C. in the presence of different combinations of DnaK, DnaJ, GrpE, GST-GmDNJ1 fusion protein, GST and bovine serum albumin (BSA). Luciferase was denatured for 10 min at 42° C. and renatured by addition of 5 mM ATP and subsequent incubation at 25° C. for 30 min. Luciferase activity was measured by using the Luciferase Assay System (Promega). Activity of luciferase in the presence of DnaK, DnaJ and GrpE (*E. coli* homologous chaperone system) was set to 100% for referencing.

GST-GmDNJ1 fusion proteins exhibited significant co-chaperone activities mimicking that of the *E. coli* DnaJ protein. On the other hand, GST or BSA did not show the same kind of activities (FIG. 11*b*).

The invention claimed is:

1. A method to protect plants or plant cells from salinity, osmotic, or dehydration stress which method comprises
   a) identifying plants or plant cells that are likely to be subjected to salinity, osmotic, or dehydration stress;
   b) modifying said plants or plant cells to produce a protein comprising a DnaJ-type J-domain;
   wherein said modifying comprises transfecting said plants or plant cells with a nucleic acid molecule that comprises control sequences that effect high expression levels in said plants or plant cells operably linked to a nucleotide sequence that encodes a protein that comprises a DnaJ-type J-domain which encoding nucleotide sequence is heterologous to said control sequences, or wherein said protein is heterologous to the plant or plant cells;
   wherein the protein further comprises, downstream from said J-domain, a DnaJ-type glycine/phenylalanine rich domain, and
   downstream from said glycine/phenylalanine rich domain a (CXXCXGXG)$_4$ (SEQ ID NO:1) zinc finger domain and wherein said protein is a Type I DnaJ protein; and
   c) subjecting said modified plants or plant cells to salinity, osmotic, or dehydration stress.

2. The method of claim 1, wherein the protein is GmDNJ1.

3. The method of claim 1 wherein said dehydration stress comprises applying water-saving cultivation method(s) to the modified plants.

4. A method to select for successful transformant plant cells or plants which method comprises
   treating said plant cells or plants with a recombinant vector comprising a nucleic acid sequence encoding, as a selectable marker, a Type I DnaJ protein comprising a DnaJ-domain, a DnaJ-type glycine/phenylalanine rich domain, and a (CXXCXGXG)$_4$ (SEQ ID NO:1) zinc finger domain said sequence operably linked to control sequences for expression; followed
   by applying salinity, osmotic, or dehydration stress to said plant cells or plants,
   whereby plant cells or plants that are resistant to said stress are selected as successfully transformed.

5. The method of claim 4, wherein the selectable marker protein is GmDNJ1.

* * * * *